United States Patent [19]

Cheng et al.

[11] Patent Number: 5,795,911
[45] Date of Patent: Aug. 18, 1998

[54] COMPOSITION FOR TREATING CONDYLOMA ACUMINATA

[75] Inventors: Shu Jun Cheng; De Chang Wang. both of Beijing, China; Yukihiko Hara, Fujieda, Japan

[73] Assignees: Cancer Institute (Hospital), Chinese Academy of Medical Sciences, Beijing, China; Mitsui Norin Co., Ltd., Tokyo, Japan

[21] Appl. No.: 835,920

[22] Filed: Apr. 10, 1997

[30] Foreign Application Priority Data

Nov. 18, 1996 [JP] Japan ............................... 8-321195

[51] Int. Cl.$^6$ ....................................................... A61K 31/35
[52] U.S. Cl. ........................................................... 514/456
[58] Field of Search ............................................... 514/456

[56] References Cited

U.S. PATENT DOCUMENTS

| | | |
|---|---|---|
| 5,135,957 | 8/1992 | Shimamura . |
| 5,159,069 | 10/1992 | Hirayama et al. ............ 536/118 |
| 5,211,944 | 5/1993 | Tempesta ..................... 424/78.08 |
| 5,576,013 | 11/1996 | Williams et al. .............. 424/423 |
| 5,605,929 | 2/1997 | Liao et al. .................... 514/456 |
| 5,648,377 | 7/1997 | Bombardelli et al. ....... 514/456 |

FOREIGN PATENT DOCUMENTS

| | | |
|---|---|---|
| 0 417 385 | 3/1991 | European Pat. Off. . |
| 22 06 570 | 9/1972 | Germany . |
| 42 11 238 | 10/1993 | Germany . |
| 2 293 548 | 4/1996 | United Kingdom . |
| WO 96 28178 | 9/1996 | WIPO . |

OTHER PUBLICATIONS

Database WPI, Week 9130, Derwent Publications Ltd., London, GB; AN 91-219271, Abstract of JP 03 141 220 A (Tsumura & Co.), Jun. 17, 1991.

Stich et al., "The effect of retinoids carotenoids and phenolics on chromosomal instability of bovine papillomavirus DNA-carrying cells", Mutation Research, vol. 241, No. 4 (1990), pp. 387–393.

Mukhtar et al., "Green Tea and Skin-Anticarcinogenic Effects", The Society for Investigative Dermatology, Inc., vol. 102,No. 1 (1994), pp. 3–7.

Hirose et al., "Inhibition of mammary gland carcinogenesis by green tea catechins and other naturally occurring antioxidants in female Sprague-Dawley rats pretreated with 7,12-dimethylbenz[α] anthracene", Cancer Letters, vol. 83, No. 1–2 (1994), pp. 149–156.

*Primary Examiner*—Raymond Henley, III
*Attorney, Agent, or Firm*—Frishauf, Holtz, Goodman, Langer & Chick, P.C.

[57] ABSTRACT

A composition for a treatment of HPV-infected Condyloma acuminata which comprises containing tea catechin as a main component. This medication has no danger of side-effects and may be easily applied to or inserted in the infected area by the patient themselves.

15 Claims, No Drawings

COMPOSITION FOR TREATING *CONDYLOMA ACUMINATA*

FIELD OF THE INVENTION

The present invention relates to a composition for treating Condyloma acuminata, or more specifically to a composition for treating Condyloma acuminata caused by human papilliomavirus, containing treating catechin as a main component.

BACKGROUND OF THE INVENTION

Condyloma acuminata is a wart detectable on the skin or mucous membrane of the genital organs of men and women, and is caused by human papilloma virus (HPV). The site of infection in men is the balanic area, coronary sulcus, foreskin, anal area, urethral meatus; and in women is the vagina, labium, anal area and urethral orifice. Clinical symptoms appear from 1–6 months, on average 3 months after infection, but usually symptoms are not noticed by the patient. This wart shows distinctive papillary or cockscomb-like tumors and has a tendency to accumulate and multiply and is usually red or reddish brown in colour. Detection of HPV in condyloma acuminata is by a method of taking tissue or a smear from the infected area and determining the DNA of the virus.

According to this method the detection rate is almost 100%. Types HPV6 and 11 of the virus are the ones most commonly detected and because HPV16 has been detected in malignant squamous cell carcinoma from cancer of the penis, cancer of the cervix and Condyloma acuminata, there is a strong possibility that HPV16 is related to the malignancy of Condyloma acuminata.

Means for a treatment of Condyloma acuminata caused by human papilloma virus which have been tried at present are by physical means such as surgical excision, electrocauterization, cryosurgery, laser therapy etc. and medication such as applications of Podophyllin, 5-Fluorouracil, Bleomycin, Interferon etc. are presently available. However surgical treatment is distressing for the patient, considering the site of infection, and with topical applications there is the concern of side-effects. Because of this no conclusive treatment is presently available.

Condyloma acuminata has a high rate of recurrence, and a complete cure is difficult unless treated constantly. Because of this a treatment which has a high degree of safety and is convenient is strongly desired.

SUMMARY OF THE INVENTION

Thus for the treatment of condyloma acuminata caused by human papillomavirus, desired is a treatment which is easy for the patient to take, for example a medication which can be applied to the affected area by the patient themselves showing good results in a relatively short period of use and having no side-effects.

DESCRIPTION OF THE INVENTION

We, the present inventors looked for a natural substance which has no side-effects, may be safely applied for a long period of time by the patient themselves and is notably effective; and after extensive testing we discovered that catechin, a component of tea which is an everyday beverage, is effective and thus the present invention was developed.

Thus the present invention relates to a composition for a treatment of Condyloma acuminata caused by human papillomavirus containing tea catechin as a main component.

DETAILED DESCRIPTION OF THE INVENTION

The tea catechin of the present invention is shown below in the general formula 1

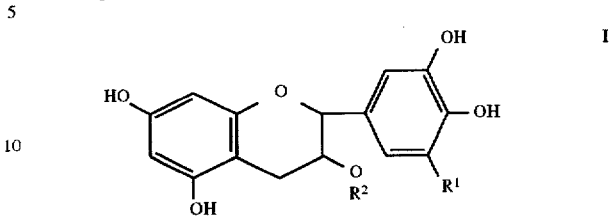

wherein $R^1$ represents H or OH and $R^2$ represents H or

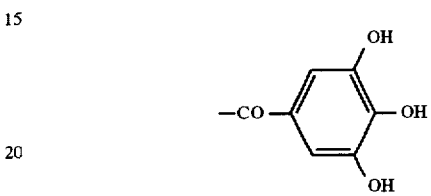

The tea catechins are more specifically, epicatechin, epicatechin gallate, epigallocatechin gallate, gallocatechin etc. (including derivatives thereof). These catechins can be used singly or two or more may be mixed together. Out of these it is particularly desirable to have (−)-epigallocatechin gallate as a main component. For example: Polyphenon 100™ (produced by Mitsui Norin Co.; Composition: (+)-gallocatechin 1.44%, (−)-epicatechin 5.81%, (−)-epigallocatechin 17.57%, (−)-epicatechin gallate 12.51%, (−)-epigallocatechin gallate 53.90%); or Polyphenon E™ (produced by Mitsui Norin Co.; Composition: (−)-epicatechin 10.8%, (−)-epigallocatechin 9.2%, (−)-epicatechin gallate 6.5%, (−)-epigallocatechin gallate 54.8%, (−)-gallocatechin gallate 4.0%).

The treatment for Condyloma acuminata of the present invention could be used for example in the form of ointment such as a cream, jelly, emulsion; or in the form of suppository such as a capsule, and usually the tea catechin component is combined with an excipient, extending agent, emulsifier, dispersing agent etc. Vaseline is suitable as a base for the ointment. For the ointment the content of tea catechin should be between 5–20% by weight, preferably between 12–18% by weight, more preferably 15% by weight. In the case of suppository the content of tea catechin should be 100–500 mg/capsule, preferably 200–300 mg/capsule, or more preferably 250 mg/capsule.

A typical usage example for the ointment is to apply directly to the infected area of the external genital organs or vagina, a vaseline cream containing 5–% by weight catechin, from once to several times everyday for a period of 1–2 months. A typical usage example for the suppository in the case where for example the infected area is the cervix or the vagina is to insert a capsule containing 100–500 mg tea catechin, from once to several times everyday for a period of 1–2 months.

There is no danger of side-effects from the treatment for condyloma acuminata with the composition of the present invention having tea catechin as the main component thereof since the main component is a natural substance derived from tea which is commonly consumed regularly, and it may be taken for long periods of time. Moreover this medication may be easily applied to or inserted in the infected area by the patient themselves. The composition of the present invention for a treatment of condyloma acuminata has a very high potential for practical use.

3

Another aspect of the invention is a method of applying an effective treating human papilloma virus-infected Condyloma acuminata amount of tea catechin to an infected area of a patient to treat human papilloma virus-infected Condyloma acuminata.

EXAMPLES

The present invention will be explained in more detail with reference to the following examples which are in no way meant to limit the scope of the invention.

Test Example 1

An ointment consisting essentially of a vaseline based vaginal lubricant containing, as the main component, tea catechin (Trade name: Polyphenon 100, produced by Mitsui Norin Co. Ltd., its main component: (−)-epigallocatechin gallate) was applied to the cervix of healthy mice (50 mice in a group) in catechin dosages of 8 mg, 15 mg, or 38 mg for a period of 7 consecutive days. After this time pathological and histological examinations were carried out and it was determined that except for a mild inflammatory reaction in the cervix of the mice of the 38 mg dose group no toxic effect was observed.

Example 1

Clinical tests of the present invention were carried out at the Cancer Institute, Chinese Academy of Medical Sciences in Beijing with a group of 15 women who had been diagnosed with HPV-infected condyloma acuminata. All patients were confirmed to have condyloma in the vulva (external genital organs), vagina and/or cervix according to clinical examination, cytologic, colposcopic and pathologic tests. Two of the fifteen patients were confirmed to be infected in two areas. Warts were from 0.2 to 2 cm in diameter.

Tests were carried out on these 15 patients using an ointment containing 10–15% of vaseline based vaginal lubricant and 5–20% of tea catechin (Trade name: Polyphenon 100, produced by Mitsui Norin Co. Ltd., crude catechin content is about 90% and its main component is (−)-epigallocatechin gallate) or using a suppository containing 100–500 mg/capsule of the above tea catechin. Applying the ointment to the external genital organs and applying the suppository to the vagina and cervix, the treatments of the present invention were used continuously once a day for about two months.

During the period of treatment examinations and colposcopic tests of the infected areas were carried out. Results obtained are shown in Table 1. As shown in the table, when the infected area completely disappeared it was judged to be cured, when 50% or more disappeared it was judged to be improved and when less than 50% or nothing disappeared it was judged there was no effect.

TABLE 1

| Infected Area | No. of Patients | Cured | Improved | No Effect |
|---|---|---|---|---|
| External genital organs | 9 | 4 | 3 | 2 |
| Vagina | 6 | 0 | 1 | 5 |
| Cervix | 2 | 1 | 0 | 1 |
| Total | 17 | 5 | 4 | 8 |
| (%) | | (29.4) | (23.5) | (47.1) |

As is evident from the table, 7 cases out of 9 (77.8%) of condyloma acuminata of the external genital organ showed a clear effect (being either cured or improved). In one case of the cervical infection the tumor completely disappeared, thus cured. During this period, apart from some patients who experienced slight pain or inflammation in the infected area and a few other patients who felt some itching, there were no obvious side-effects observed.

Example 2

The clinical tests at the Cancer Institute, Chinese Academy of Medical Sciences in Beijing were conducted in the same manner as in Example 1 with a group of 33 female patients diagnosed with HPV-infected condyloma acuminata. In this group, 8 of the patients were infected in two areas. Results are shown in Table 2. As is evident from the table, 92% of condyloma acuminata of the external genital organs and 70% of the vaginal condyloma acuminata was cured or improved, and in the case of the cervical condyloma acuminata, all cases were cured. 25 cases out of 41 cases showed the result as cured and the curing ratio was 61%.

TABLE 2

| Infected Area | No. of Patients | Cured | Improved | No Effect |
|---|---|---|---|---|
| External genital organs | 26 | 18 | 6 | 2 |
| Vagina | 10 | 2 | 5 | 3 |
| Cervix | 5 | 5 | 0 | 0 |
| Total | 41 | 25 | 11 | 5 |
| (%) | | (61.0) | (26.8) | (12.2) |

Example 3

The clinical test at the Cancer Institute, Chinese Academy of Medical Sciences in Beijing was conducted in the same manner as in Example 1 with a group of 22 female patients diagnosed with HPV-infected condyloma acuminata. Results are shown in Table 3. As is evident from the table, out of 16 cases of condyloma acuminata of the external genital organs 7 were cured and 6 improved; a total of 13 (81.3%) being effected. In the case of condyloma acuminata of the vagina, out of 6 cases 3 were cured and 2 were improved; a total of 83.3% was confirmed to be effected.

TABLE 3

| Infected Area | No. of Patients | Cured | Improved | No Effect |
|---|---|---|---|---|
| External genital organs | 16 | 7 | 6 | 3 |
| Vagina | 6 | 3 | 2 | 1 |
| Total | 22 | 10 | 8 | 4 |
| (%) | | (45.5) | (36.4) | (18.2) |

The entire disclosure of Japanese Patent Application No. 8-321195 filed on Nov. 18, 1996 including specification, claims and summary are incorporated herein by reference in its entirety.

What is claimed is:

1. A method of treating Condyloma acuminata caused by human papillomavirus, comprising applying to an infected area on a human a composition which comprises a tea catechin as a main component in an amount effective for treating Condyloma acuminata.

2. The method according to claim 1, wherein the composition is in the form of an ointment or a suppository.

3. The method according to claim 1, wherein said composition is in the form of an ointment having 5–20% by weight of tea catechin.

4. The method according to claim 1, wherein said composition is in the form of a suppository having 100–500 mg of the tea catechin in a capsule.

5. The method according to claim 1, wherein said tea catechin comprises (−)-epigallocatechin.

6. The method according to claim 3, wherein the tea catechin is in an amount of 12–18% by weight.

7. The method according to claim 4, wherein the tea catechin is in an amount of 15% by weight.

8. The method according to claim 3, wherein the capsule contains 200–300 mg of the tea catechin.

9. The method according to claim 4, wherein the capsule contains 250 mg of the tea catechin.

10. The method according to claim 3, wherein the ointment contains vaseline as a base to form a cream.

11. The method according to claim 3, wherein the ointment is applied to external genital organs.

12. The method according to claim 4, wherein the suppository is applied to the vagina of a human.

13. The method according to claim 1, wherein the infected area is the vagina.

14. The method according to claim 1, wherein the infected area is an external genital organ.

15. The method according to claim 1, wherein the infected area is the cervix.

* * * * *

UNITED STATES PATENT AND TRADEMARK OFFICE
CERTIFICATE OF CORRECTION

PATENT NO. : 5,795,911
DATED : August 18, 1998
INVENTOR(S) : CHENG et al

It is certified that error appears in the above-identified patent and that said Letters Patent is hereby corrected as shown below:

Column 5, line 8 (Claim 7): delete "4" and insert --3--.

Column 5, line 10 (Claim 8): delete "3" and insert --4--.

Signed and Sealed this

Twenty-third Day of November, 1999

Attest:

Q. TODD DICKINSON

*Attesting Officer*    *Acting Commissioner of Patents and Trademarks*